United States Patent
Shofner et al.

(10) Patent No.: US 6,735,327 B1
(45) Date of Patent: May 11, 2004

(54) COLOR AND TRASH MEASUREMENTS BY IMAGE ANALYSIS

(75) Inventors: Frederick M. Shofner, Knoxville, TN (US); Christopher K. Shofner, Knoxville, TN (US)

(73) Assignee: Shofner Engineering Associates, Inc., Knoxville, TN (US)

( * ) Notice: Subject to any disclaimer, the term of this patent is extended or adjusted under 35 U.S.C. 154(b) by 619 days.

(21) Appl. No.: 09/663,502

(22) Filed: Sep. 15, 2000

Related U.S. Application Data
(60) Provisional application No. 60/221,104, filed on Jul. 27, 2000, provisional application No. 60/182,731, filed on Feb. 15, 2000, and provisional application No. 60/154,527, filed on Sep. 16, 1999.

(51) Int. Cl.[7] ................................................. G06K 9/00
(52) U.S. Cl. ........................ 382/111; 382/165; 382/218
(58) Field of Search .............................. 382/100, 111, 382/141, 143, 162, 165, 209, 217, 218, 224; 356/238.1; 700/130; 348/88

(56) References Cited

U.S. PATENT DOCUMENTS

| | | |
|---|---|---|
| 3,591,294 A | 7/1971 | Neil |
| 4,093,991 A | 6/1978 | Christie, Jr. et al. |
| 4,529,308 A | 7/1985 | Rife |
| 4,672,676 A | 6/1987 | Linger |
| 4,744,035 A | 5/1988 | Hashim |
| 4,758,960 A | 7/1988 | Jung |
| 4,788,650 A | 11/1988 | Willis et al. |
| 5,253,306 A | 10/1993 | Nishio |
| 5,285,383 A | 2/1994 | Lindsey et al. |
| 5,639,955 A | 6/1997 | Anthony |
| 5,774,177 A | 6/1998 | Lane |
| 5,774,574 A | 6/1998 | Hoki |
| 5,799,105 A | 8/1998 | Tao |
| 5,829,487 A | 11/1998 | Thomas et al. |
| 5,841,892 A | 11/1998 | McGrath et al. |
| 5,897,620 A | 4/1999 | Walker et al. |
| 5,938,607 A | 8/1999 | Jago et al. |
| 6,014,451 A | 1/2000 | Berry et al. |
| 6,052,182 A | 4/2000 | Irick, Sr. et al. |
| 6,085,180 A | 7/2000 | Beer et al. |
| 6,085,227 A | 7/2000 | Edlund et al. |
| 6,243,166 B1 | 6/2001 | Aemmen .................... 356/430 |
| 6,415,045 B1 * | 7/2002 | Quigley et al. ............. 382/111 |
| 6,567,538 B1 * | 5/2003 | Pelletier .................... 382/111 |

FOREIGN PATENT DOCUMENTS

| | | |
|---|---|---|
| EP | 0 844 581 A2 | 5/1998 |
| WO | WO 98/00243 | 1/1998 |
| WO | WO 99/21118 | 4/1999 |
| WO | WO 01/20321 | 3/2001 |

OTHER PUBLICATIONS
Partial International Search in PCT/US 00/25470 (Annex to Invitation to Pay Additional Fees mailed Feb. 15, 2001).

* cited by examiner

*Primary Examiner*—Phuoc Tran
(74) *Attorney, Agent, or Firm*—Carter Schnedler & Monteith, P.A.

(57) ABSTRACT

An ultrasonic diagnostic imaging system is provided which aid in the diagnosis of patient conditions by providing access from the ultrasound system to a library of reference ultrasonic images. The image library is cataloged in accordance with an image characteristic such as the type of examination, the part of the body or the type of pathology shown in the image, and the images of the library are accessed in accordance with these characteristics. The image library may he remotely located and accessible by a number of ultrasound systems over a network, or it may be located on the ultrasound system itself such as on a system disk drive. In a preferred embodiment reference images are concurrently displayed with patient images to aid in discerning the patient's condition.

21 Claims, 14 Drawing Sheets

COLOR AND TRASH MEASUREMENTS BY IMAGE ANALYSIS

CROSS-REFERENCE TO PROVISIONAL PATENT APPLICATIONS

The benefit of U.S. Provisional Patent Application Ser. No. 60/154,527, filed Sep. 16, 1999; Ser. No. 60/182,731, filed Feb. 15, 2000; and Ser. No. 60/221,104, filed Jul. 27, 2000 is claimed.

BACKGROUND OF THE INVENTION

The invention relates generally to fiber quality measurements for cotton classing and, more particularly, to image-based instrument measurements of Color and Trash.

Cotton standards are supported by the United States Department of Agriculture (USDA) through its Agricultural Marketing Service (AMS). Cotton standards, and the corresponding classing of cotton, are of great importance in determining the market value of a particular bale of cotton, as well as determining suitability of a particular bale of cotton from a gin for subsequent processing at a particular mill in view of the products and processes of that mill. AMS is responsible for preparing and maintaining such cotton standards and does so in its Standards Section located in Memphis, Tennessee.

In 1923, the United States and nine European countries entered into the Universal Cotton Standards Agreement. From that time, up until approximately 1965, USDA/AMS cotton classing "measurements" based on the Universal Standards were made entirely by humans. The human measurements included "grade," "extraneous matter" (such as bark and grass), "preparation" (which relates to smoothness of the sample) and "staple length" (long fiber content). Instrument-based cotton classing was introduced in 1965, beginning with micronaire, followed in 1980 by High Volume Instruments (HVI), which added measurements of length and strength. HVIs currently measure the fiber qualities of Micronaire, Length, Strength, Color and Trash. Instruments for measuring Color (Rd, +b and +a, which refer to "reflectiveness," "yellowness" and "redness") and Trash (% Area) have also been developed, but Human Classer measurements of Color and Trash are still generally employed because of certain deficiencies in these methods.

Prior to 1993, Classer's Grade was a combination of color and leaf trash. In USDA/AMS classing, the human Classer now separately calls a color grade and a leaf grade. These Classer's calls for color and leaf grade are still the official measurements, along with a Classer's call about "Extraneous Matter" and "Preparation." Although currently unofficial, instrumental measurements of Color and Trash, as well as exploratory measurements of Short Fiber Content are made, however deficient, both to satisfy mill requests for the information and to lay the foundation and to create demand for improvements.

The Classer measurements of color, trash, preparation and extraneous matter are primarily visual, and measurements of staple length are both tactile and visual. It is appropriate to call all human classifications "measurements" in a broad sense. This is because Classers are rigorously trained to compare their observations to cotton standards immediately available to them. That is, they measure first, by comparison, then put the sample into a "class." If a Classer has any doubt about a classing call, the Classer can, sample in hand, go to a set of standards boxes to refresh the Classer's memory to improve the "call" by comparison to the standards for Grade and Staple.

Considering in particular the current methods of human visual fiber quality measurements, the Classer holds a sample from a bale and visually examines its appearance in good, meaning standardized, illumination. Making the measurements of Color Grade and Leaf Grade physiologically and psychologically amounts to comparing the images falling on the retinas and perceived by the brain with images from memory or, for confirmation, images from physical standards. The procedures of making such measurements are learned in extensive training. "Classer's Call" means that the Classer has measured the object and judged it to fall within or near to a standard or, if not, he or she comments why.

SUMMARY OF THE INVENTION

In embodiments of the invention, an optical imaging device having a defined object field of view acquires an image for classifying an unknown sample of cotton. The unknown sample of cotton is placed in the object field of view, as well as at least one reference material. As a result, the optical imaging device acquires images of both the unknown sample of cotton and the reference material in the same field of view, at the same time and under the same measurement conditions.

In an instrument classification embodiment, an instrumental "call" or classification of the sample under test is made without reconstructing an image of the object field for human viewing.

In a human classification embodiment, the image of the entire object field, including the sample under test and at least one reference material, is reconstructed for human classification, either locally or remotely. When the image file is transferred over the internet to a remote location, we refer to the embodiments as "Internet Classing."

Inclusion of at least one reference material, having known and traceable optical properties in the object field is an important feature in both embodiments, and overcome the deficiencies of prior art methods. It is particularly advantageous to use reference materials which are similar to the samples under test. Thus cottons, whose color or trash properties are established by AMS or others, are included as reference materials. In the instrument classification, algorithms match the unknown to the knowns.

Embodiments of the invention can employ, as the optical imaging device, a high quality color scanner intended for office or graphics arts use in scanning documents. In the context of the invention, the inclusion of at least one reference material in the object field is not intended to refer to the usual and conventional calibration "strip" included in such color scanners. Such a calibration "strip" is internal to the scanner, and is generally employed to calibrate the intensity of the illumination within the scanner. The internal scanner calibration "strip" is not part of the acquired image data.

DETAILED DESCRIPTION

Figure 1:
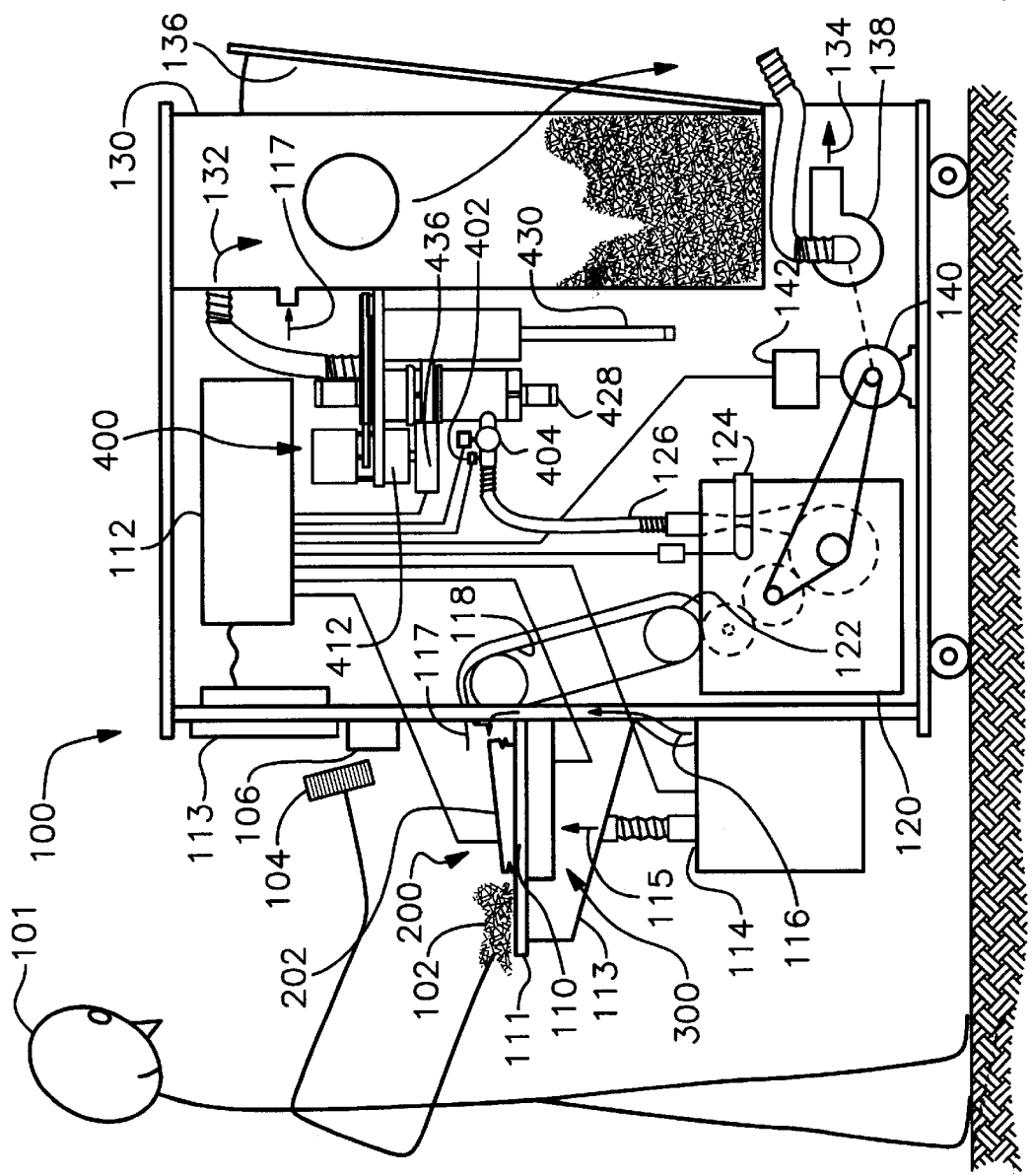
FIG. 1 is an overview of a machine embodying the invention, which machine measures cotton samples to produce multiple data products, including images, and additionally internally and ultra-rapidly conditions samples.

Referring first to FIG. 1, the invention is embodied in a stand-alone instrument 100 which measures cotton samples to produce multiple data products, including images, and additionally internally and ultra-rapidly conditions samples. Instrument 100 is a robust, stand-alone platform upon which fiber quality measurement modules are placed to effect generation of multiple data products. By including internal, ultra-rapid sample conditioning, the instrument 100 eliminates the need for expensive conditioned laboratory space. The machine 100 thus does the work of several other instruments and an expensive laboratory air conditioning system, and does that work in the challenging ginning environment.

System Overview

Operator 101 in FIG. 1 selects a "Classer's Sample" having an estimated weight of approximately 15 grams of sample 102. Such a 15-gram sample is typically 5 inches (12.7 cm) wide×8 inches (20.32 cm) long×1 inch (2.54 cm) thick, when uncompressed. The operator "swipes" permanent bale identification (PBI) tag 104 through bar code reader 106, and prepares and introduces sample 102 into recessed conditioning/test chamber 110 of "stable table" top 111, when pressure/distribution plate 202 is retracted. (See also FIG. 2.) The operator 101 then initiates automatic conditioning/testing by causing pressure/distribution plate 202 to move over sample 102 in the recessed conditioning/ testing chamber 110, compressing the sample to a thickness of less than 3 mm. Directed by a process control computer 112, the machine 100 then automatically effects "Ultra-Rapid Conditioning" in module 200, and additionally effects testing of the sample 102 for Color and Trash in module 300. (Operator 101 can monitor and control the progress of conditioning/testing, and of all other operations, as well as examine the data products produced, stored, and communicated by system 100 via computer 112 and touch-screen display 113.)

Conditioned gas for conditioning sample 102 in conditioning/testing chamber 110 and for transporting and processing sample 102 in subsequent steps is provided by air conditioning module 114. Air conditioning module 114 provides a conditioned gas flow 116 having controlled environmental parameters such as Relative Humidity of 65%, dry bulb Temperature of 70° F. (21° C.), and flow rates of 200 CFM (5.7 m³/min). Conditioned gas flow 116 is conducted to the entrance 117 for both the individualizer 120 flow 122 and for the sample conditioning module 200. In a variation, gas flow 116 is split into two components, one having the fixed, standard parameters just described and a second having variable humidity, temperature, flow rate and pressure and which variable parameters are automatically controlled by a separate controller within air conditioner 114, and which parameter values are determined in accordance with optimally conditioning sample 102 within conditioning/testing chamber 110.

In overview, sample 102, having been manually or automatically placed in recessed conditioning/testing chamber 110, with the pressure/distribution plate assembly 202 over it, is ultra-rapidly "conditioned" from above window 204 and "tested" for Color and Trash below it. Sample 102 may also be tested for moisture content in chamber 110, according to which data air conditioning module 114 is caused to optimally condition sample 102 under control of computer 112.

As a practical matter, the nominal transverse dimensions of the conditioning module 200 and Color and Trash testing module 300 are 8.5×11 inches (21.59×27.94 cm), the size of standard paper in the United States. This is because the Color and Trash module 300 is based on available high quality and high resolution color scanners intended for office and graphics arts use in scanning documents. However, any device for acquiring the raw image files and any transverse dimensions may be employed.

Figure 3:
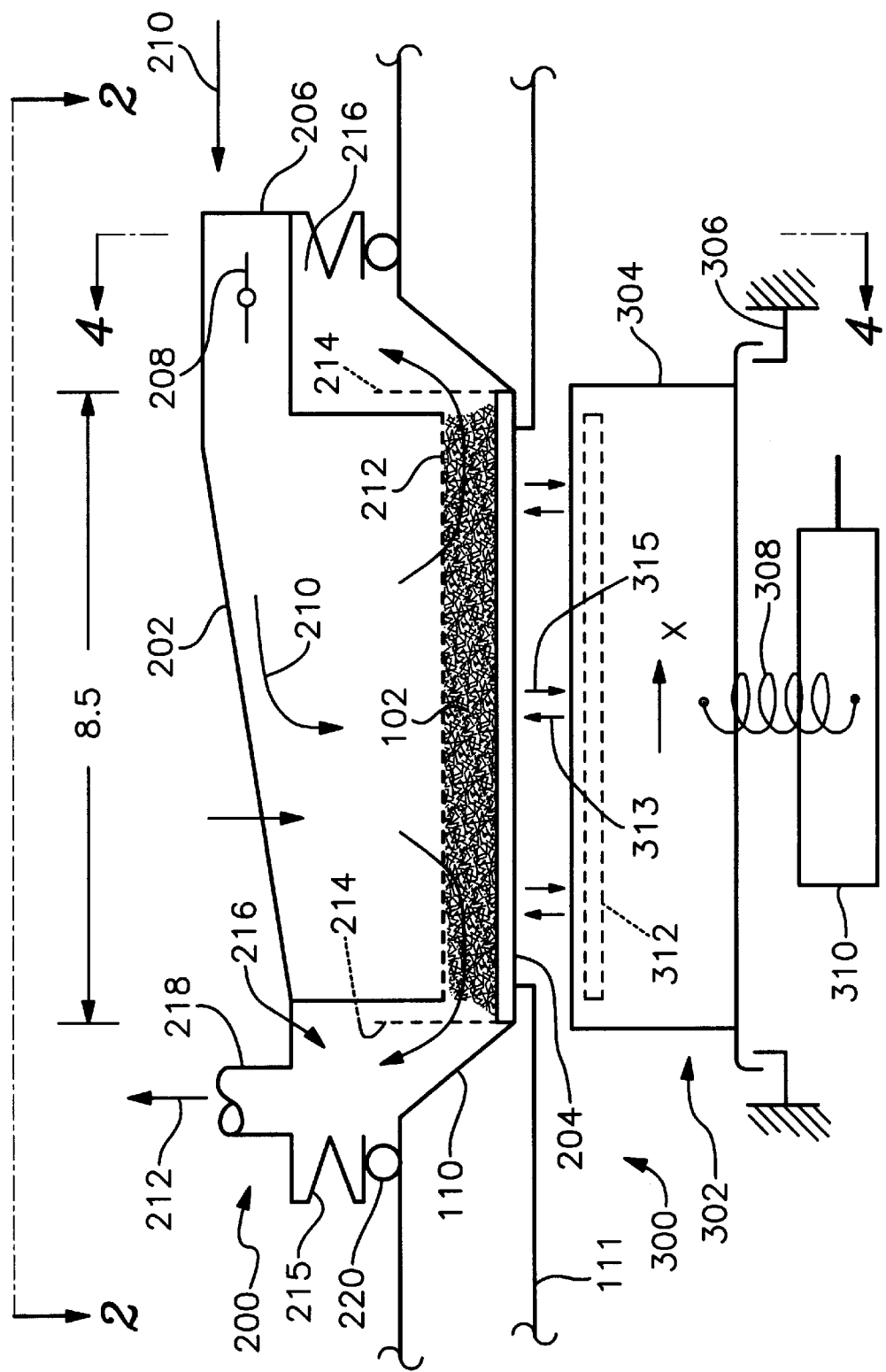
FIG. 3 is a side view of the Ultra-Rapid Conditioning module and the Color and Trash module.

By way of example, there are two alternative embodiments involving primarily valve 208 (FIG. 3) and perforated plate 212 (FIG. 3). Downward force on sample 102 in recessed conditioning/testing chamber 110 is important for the Color and Trash measurements. However, when sample conditioning is not required, as it is not for most color and trash measurements, sample pressure is applied by simpler mechanical means. Mechanical means may also be used to compress sample 102 when suction forces are inappropriate.

In the first alternative for applying pressure to the sample 102 under test, valve 208 in FIG. 3 is open while conditioned air from module 114 is delivered to condition sample 102. In this first alternative, the holes in relatively thick and rigid perforated plate 212 are relatively large and the flow rate delivered for conditioning is high. After typically ten seconds, valve 208 partially closes and restricts flow 210 into Ultra-Rapid Conditioning module 200, thus causing a strong negative pressure or suction to be developed within pressure distribution plate 202. This suction causes atmospheric pressure to force plate 202 downward onto sample 102. Bellows 215 and seals 220 enable the downward movement and the suction, respectively. There is also an equal and opposite upward atmospheric pressure force on sample 102 exerted by window 204. Sample pressure is important for the Color and Trash measurement.

In the second, simpler alternative, there is no valve 208, and perforated plate 212 is preferably thinner and has fewer and/or smaller holes. These smaller holes in plate 212 inherently limit the flow 210 and thus develop the suction force across perforated plate 212, directly. Open areas of the order of 10% represent a satisfactory compromise between downward force, for Color and Trash measurements by module 300, and flow rate 210, for Ultra-Rapid Conditioning. This second alternative also enables parallel operations for Ultra-Rapid Conditioning processing by module 200 and for Color and Trash testing by module 300.

The substantially simultaneous Ultra-Rapid Conditioning by module 200 and image acquisition testing by module 300 lasts less than one minute and can be as short as approximately ten seconds, depending on scanner resolution chosen and how close in moisture content the selected sample 102 lies to an acceptable value, such as 7.3% for cotton. Such ultra-rapid sample conditioning is particularly useful as preconditioning for subsequent testing.

At the completion of the conditioning/testing cycle, pressure/distribution cover 202 (or pressure plate (not shown) in the event Ultra-Rapid Conditioning is not employed) is opened. The cover 202 may be opened manually, or automatically upon receipt of a signal from computer 112. Sample 102, which is now conditioned for further processing and testing, is automatically or manually moved onto belt 118 for quick transport to an individualizer 120, which thoroughly opens, i.e., "individualizes," sample 102 into its various constituent entities, fibers, neps, trash, seed coat fragments, sticky points, microdust, and the like. A suitable individualizer is disclosed in Shofner et al U.S. Pat. No. 5,890,264. An alternative is for individualizer 120 to also clean sample 102 by removing trash, microdust and other foreign matter. However, in the disclosed embodiment almost all of the individualized entities are transported in the same transport flow stream.

This processing by individualizer 120 causes the thoroughly individualized entities to be entrained in or transported by about 120 CFM (3.4 m$^3$/min) of conditioned air flow 122 such that the fiber and other entity concentrations transported by the gas flow at the output 126 of individualizer 120 are very low. Accordingly, the Nep content of thus-individualized sample 102 is measured with a nep sensor 124 which advantageously is built into the individualizer 120. A suitable nep sensor 124 is as disclosed in Shofner et al U.S. Pat. No. 5,929,460.

Sample 102, whose weight was guessed by operator 101 at approximately 15 grams, is at the output 126 of individualizer 120 in a highly opened, individualized state that simulates the state of fiber in important textile processing machines, especially carding. Accordingly, the state of the fiber is ideal for testing the individual fibers and other entities in the gas flow 122. One such test is the Nep test made by nep sensor 124. Other tests are Micronaire-Maturity-Fineness (MMF), effected by module 400. For Neps and for MMF, it is required that the sample weight be known, not guessed, and sample masses of nominally ten grams are commonly used for both tests. The sample weight can be determined prior to or after the testing using known analytical balance technologies. Post testing weighing can be automated.

The system aspects of the disclosed embodiment can be summarized:

1. Common flow;
2. Optimal sequence for sample tests, from surface measurement of Color and Trash to volume or weight measurements of Neps and Micronaire based on guessed weight or on precise weight;
3. Ideal sample state for simulations of actual processing (e.g., cleanability, processability, spinnability); and
4. Automatic except for selecting and introducing classer's sample, thus eliminating operator effort and errors. System and methods can be extended to complete automation.

Image-Based Color and Trash Measurements

Figure 2:
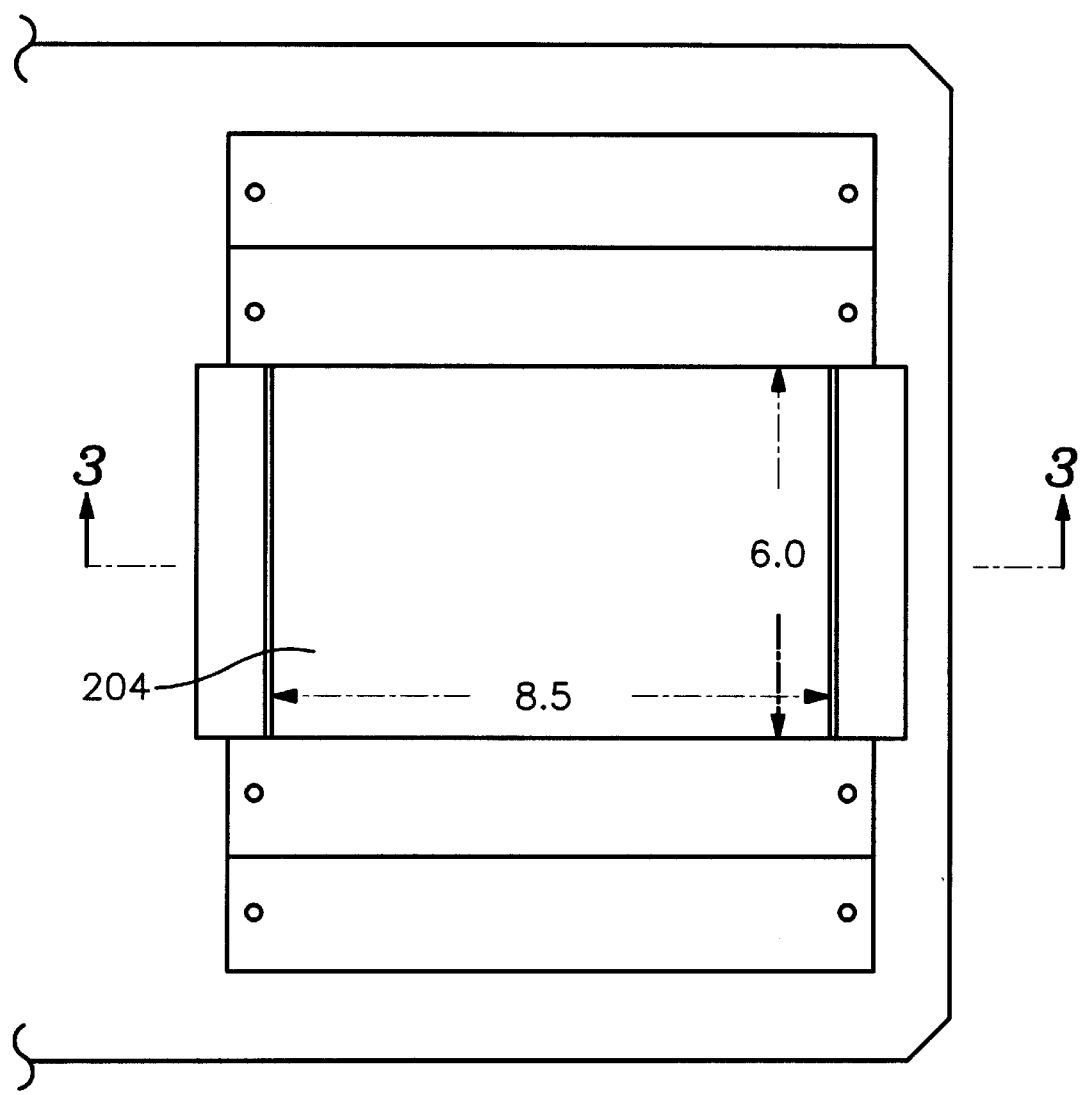
FIG. 2 is a top view of the Ultra-Rapid Conditioning module and the Color and Trash module of the machine of FIG. 1, without a pressure/distribution cover plate in place.
Figure 4:
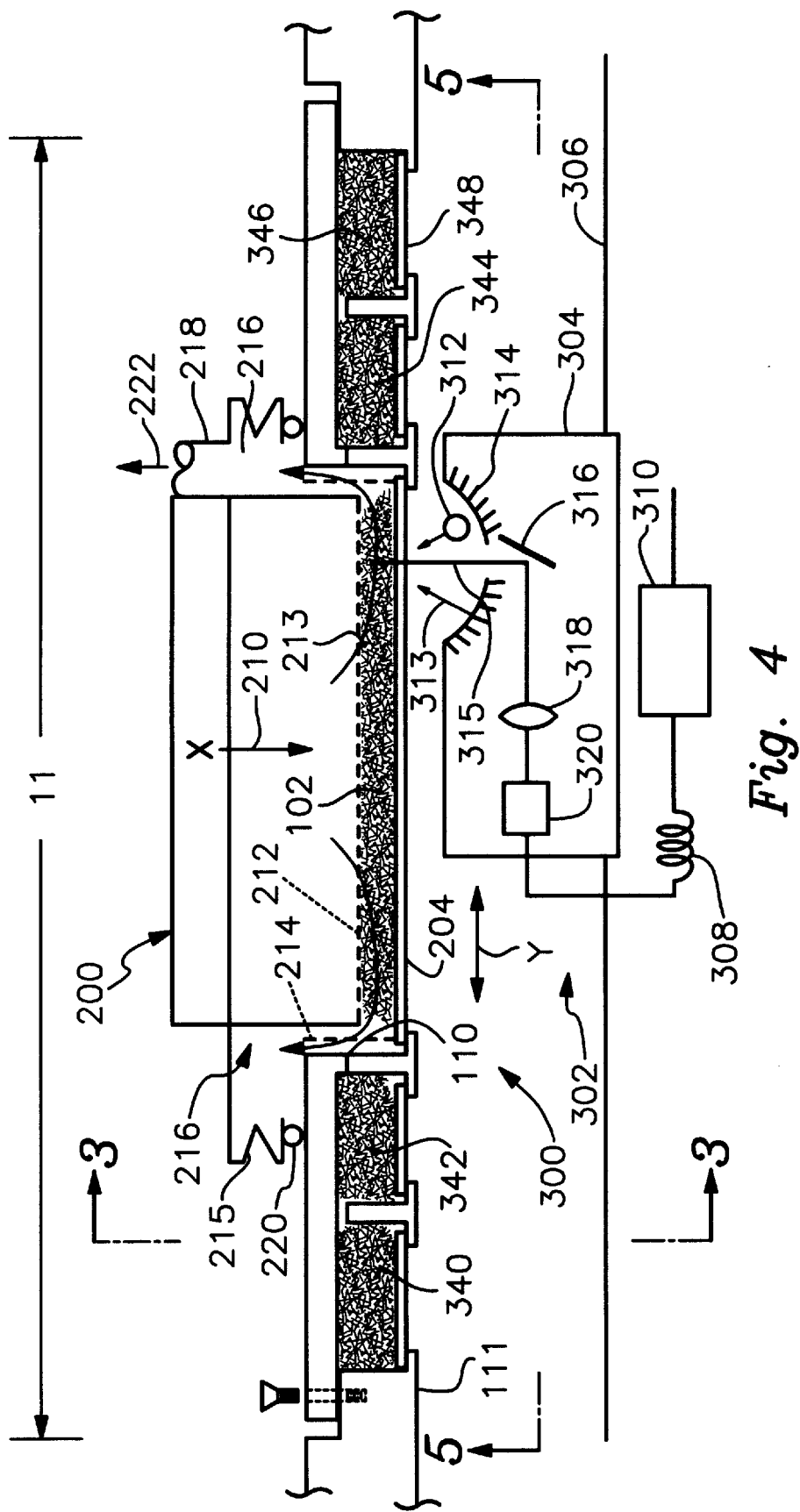
FIG. 4 is an end view of the Ultra-Rapid Conditioning module and the Color and Trash module.
Figure 5:
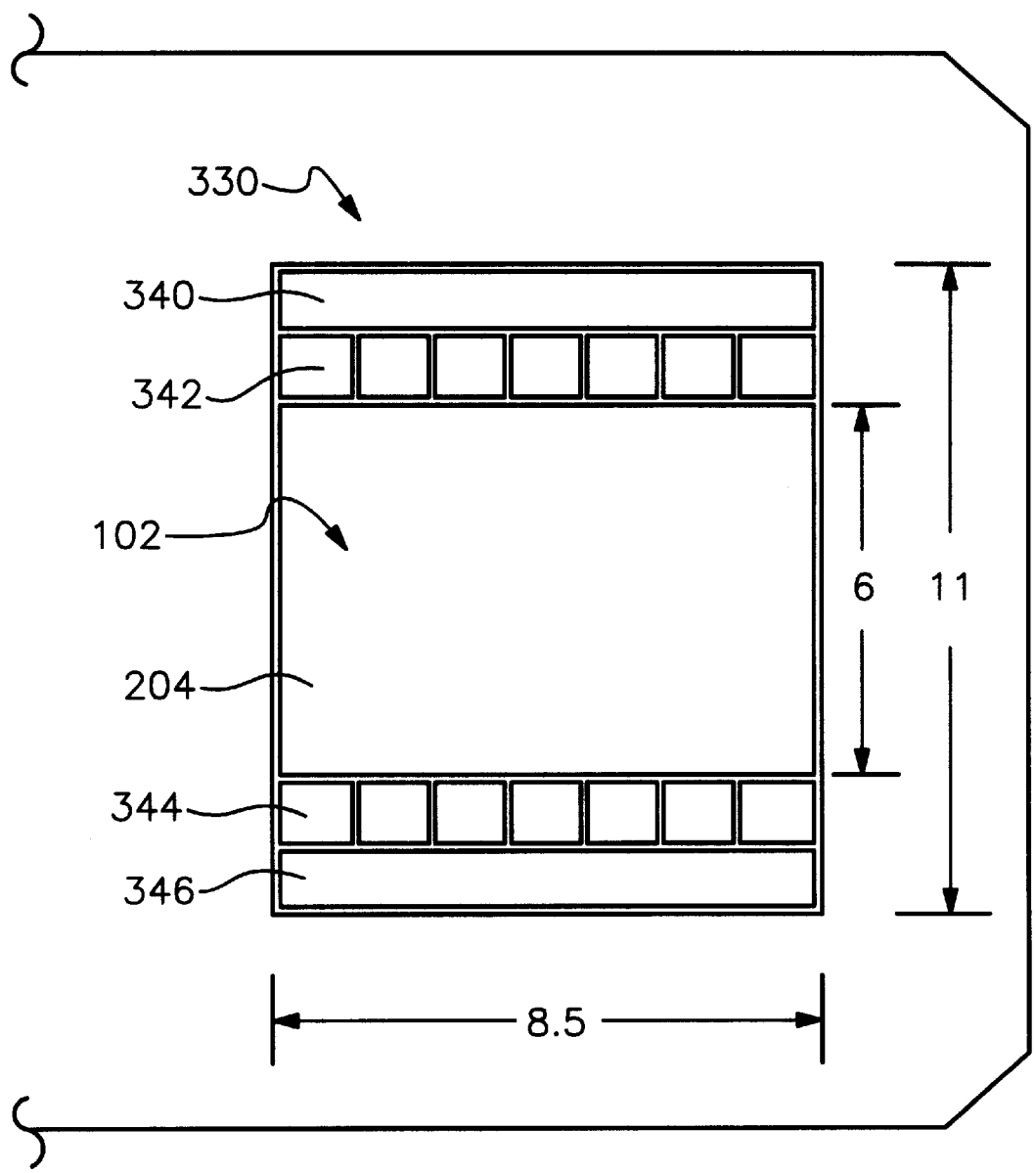
FIG. 5 is a bottom view of the Ultra-Rapid Conditioning module and the Color and Trash module, showing the optical imaging device field of view.

FIGS. 2–5 show both the Ultra-Rapid Conditioning module 200 and the Color and Trash module 300 of the machine 100 of FIG. 1. FIG. 2 is a top view, without pressure/distribution cover plate 202; and FIG. 5 is a bottom view. FIGS. 3 and 4 are side and end views, respectively.

Figure 6:
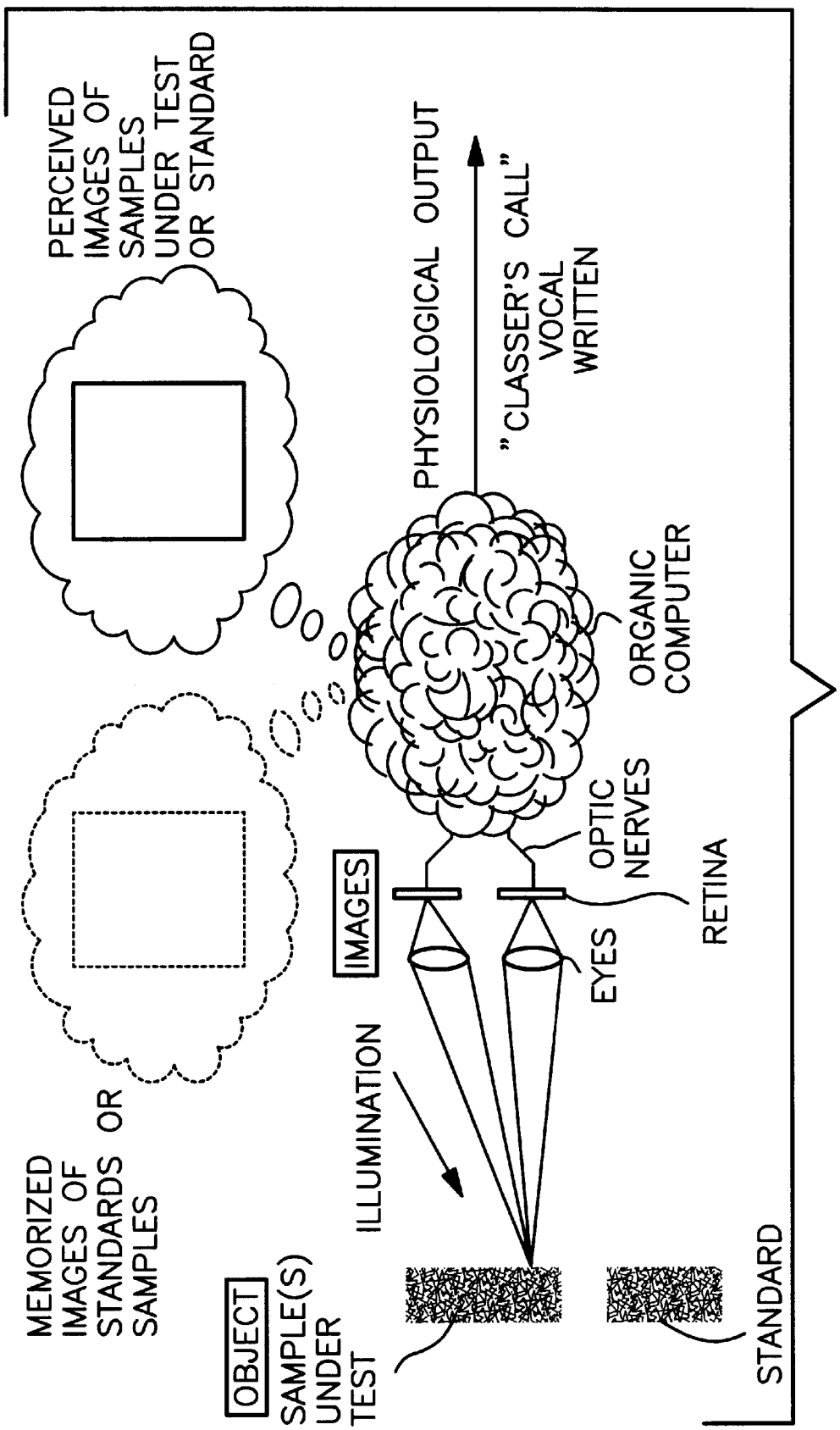
FIG. 6 represents the manner in which a human Classer measures fiber quality.
Figure 7:
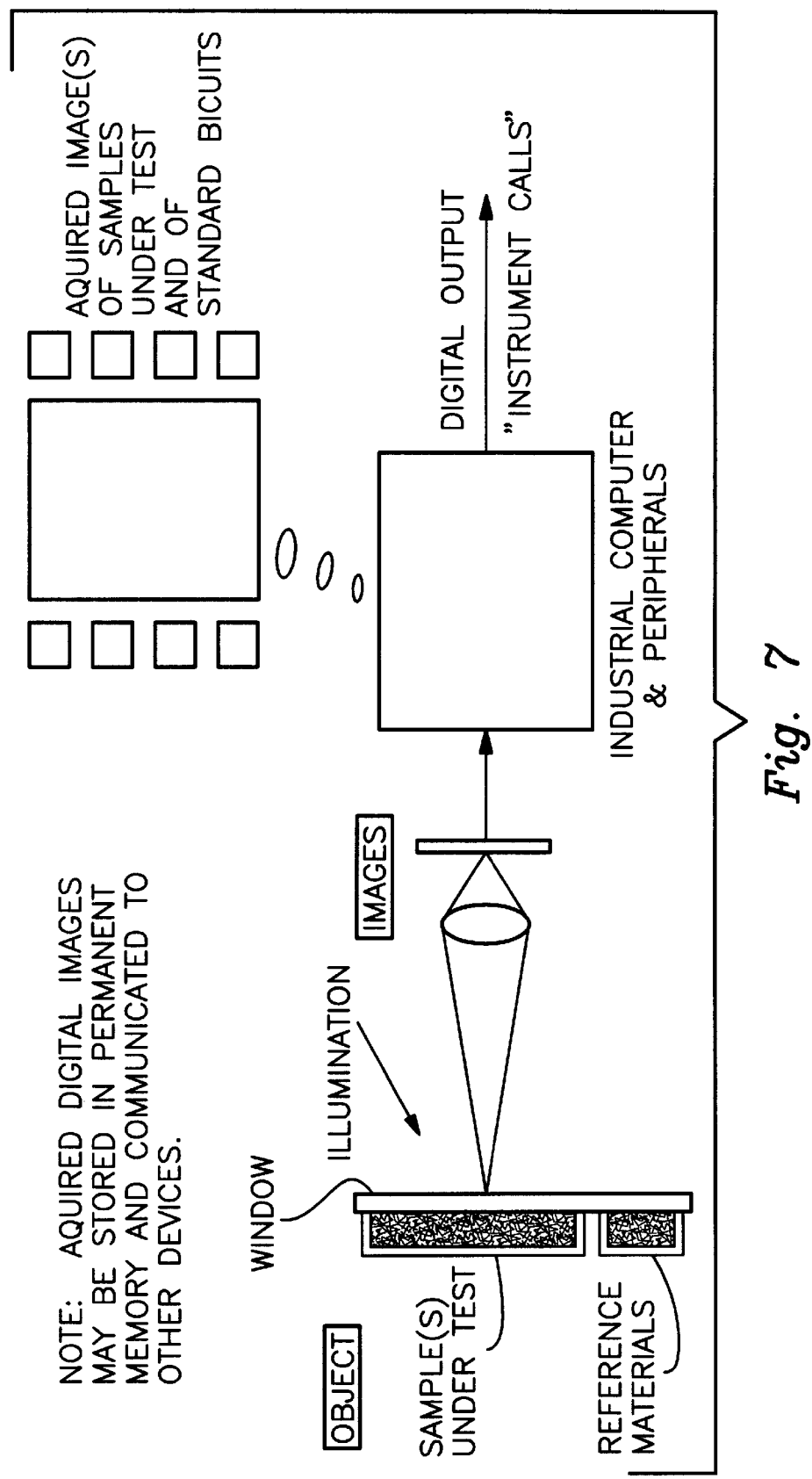
FIG. 7 represents image based measurements of fiber quality.
Figure 8:
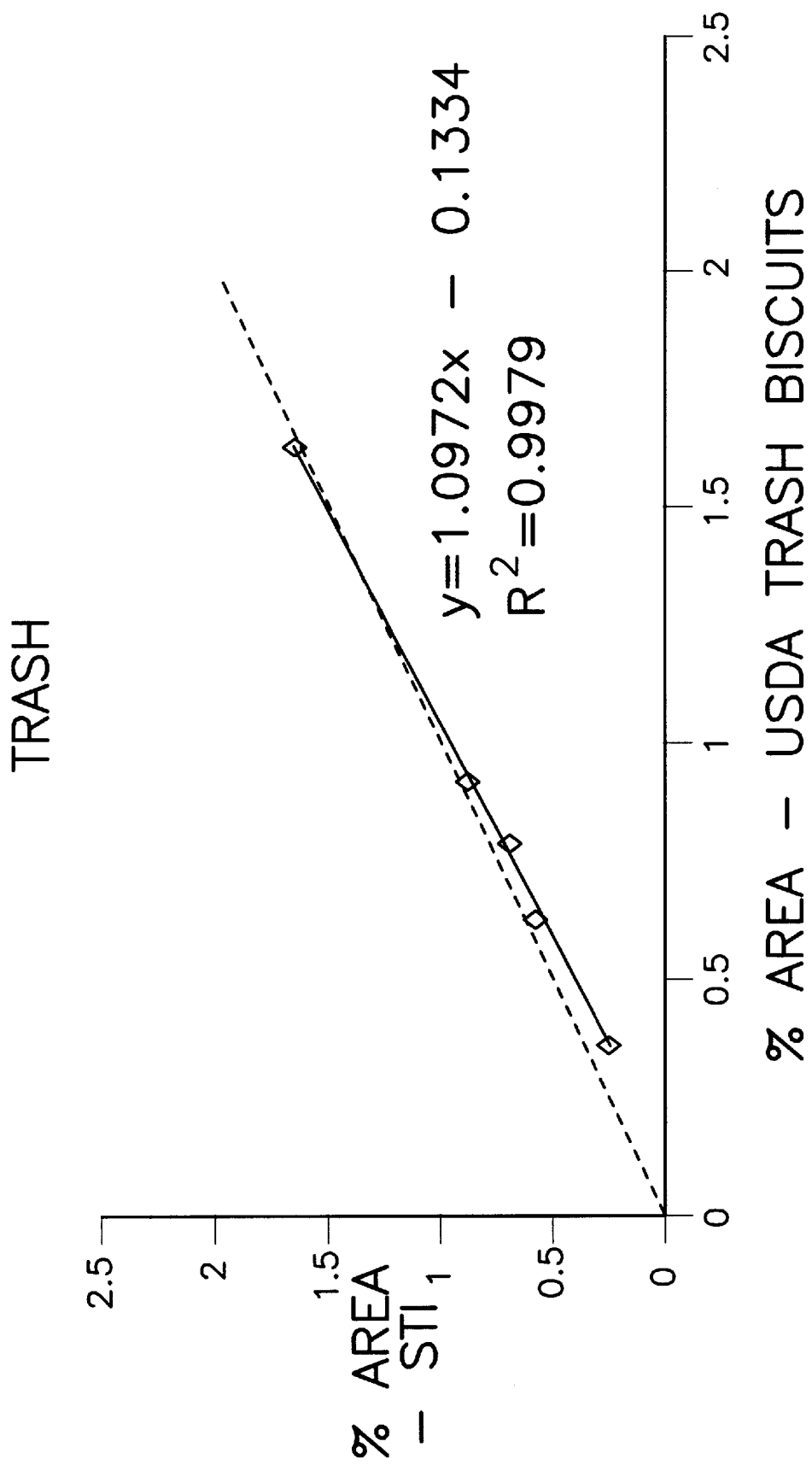
FIG. 8 is a graph depicting Trash-measurement performance of an embodiment of the invention.
Figure 9:
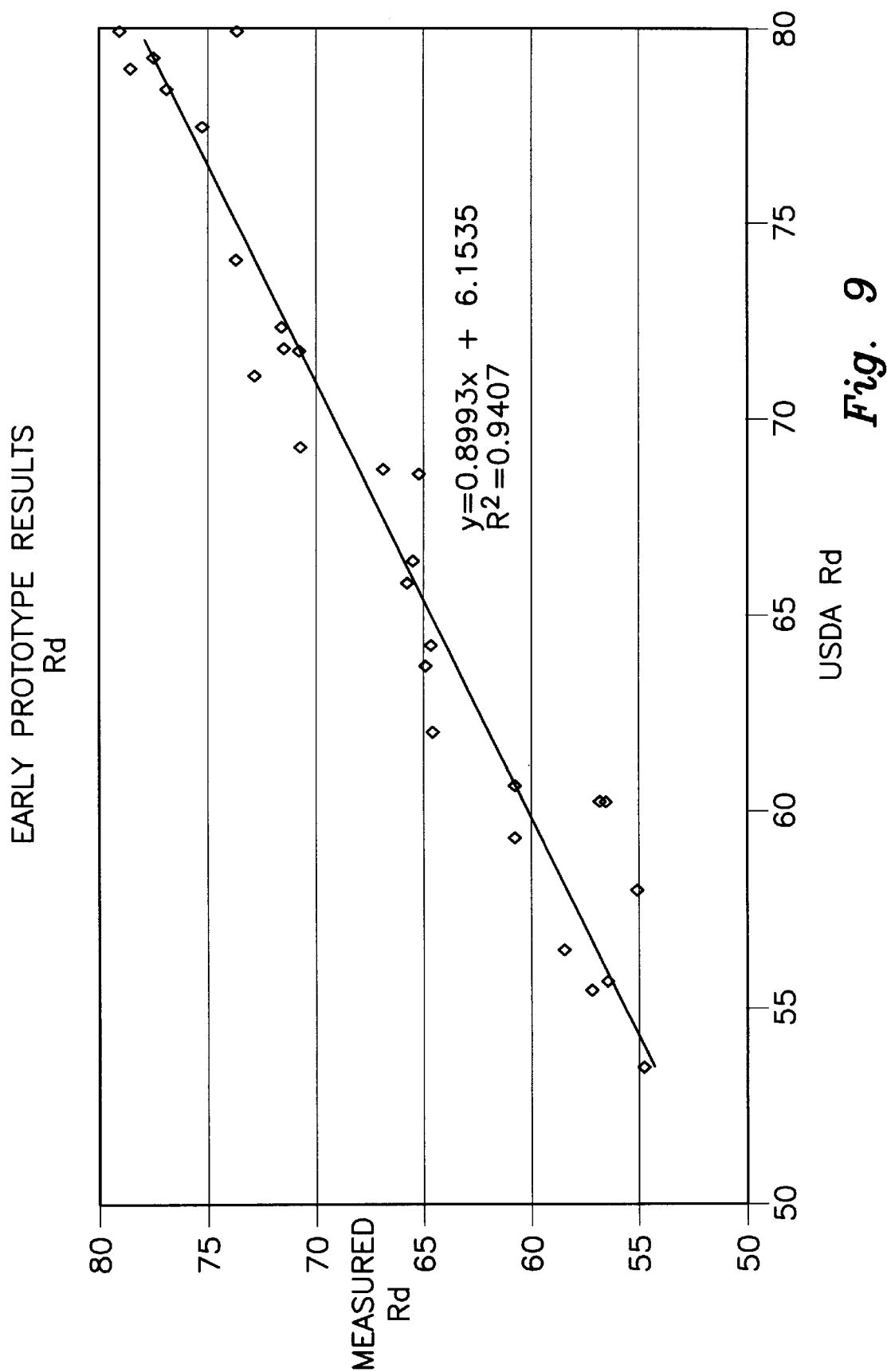
FIG. 9 is a graph depicting color (Rd) measurement performance of an embodiment of the invention.
Figure 10:
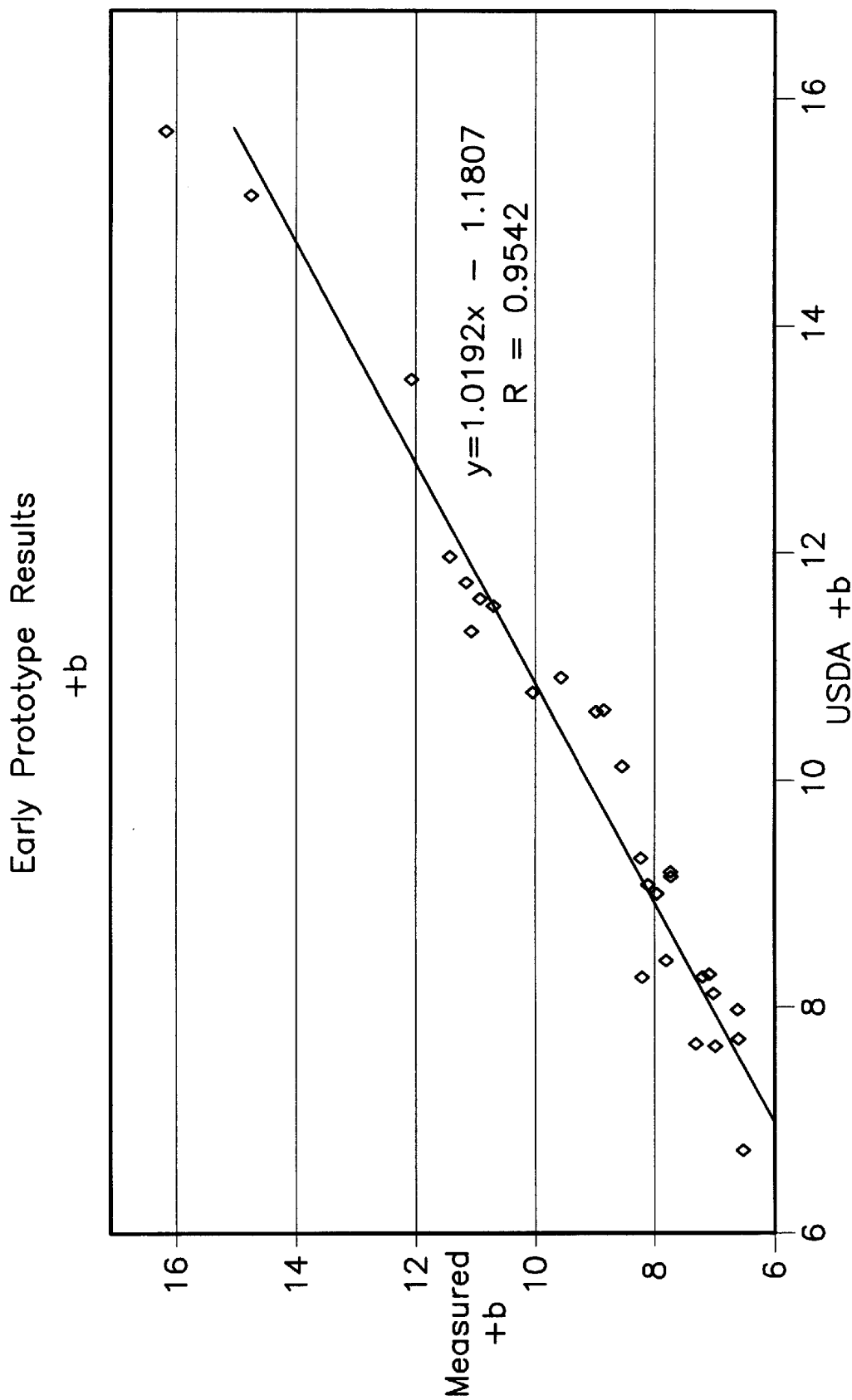
FIG. 10 is a graph depicting color (+b) measurement performance of an embodiment of the invention.
Figure 11:
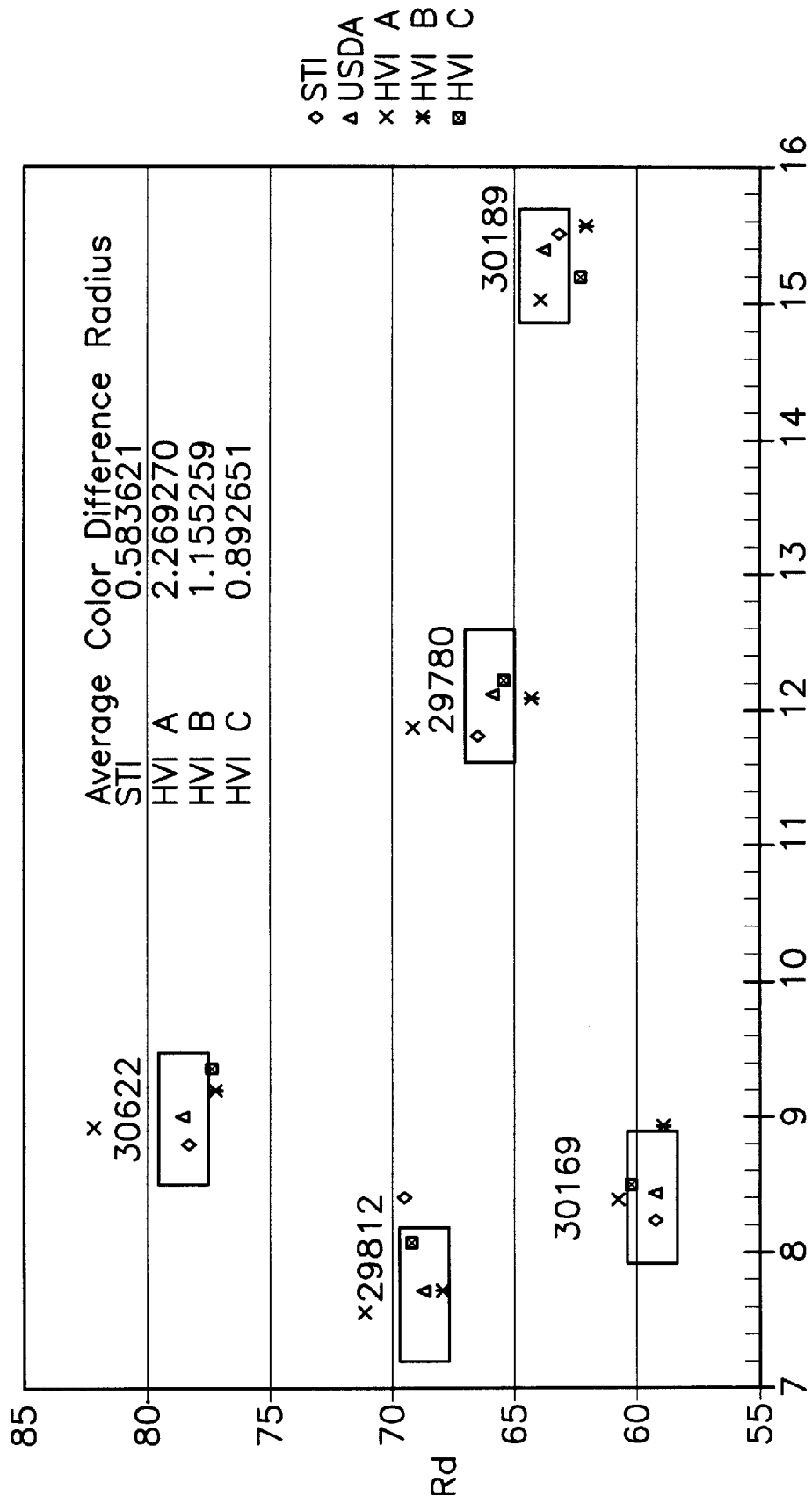
FIG. 11 is a graph depicting color (Rd us +b) measurement performance of an embodiment of the invention.

FIGS. 6 and 7 more generally disclose embodiments of the invention for measuring Color and Trash, including Extraneous Matter. Thus the Color and Trash module 300 is an image-based system which improves the measurements of these basically important fiber qualities over current methods. Preparation can also be measured, if that data product is needed.

Comparing FIGS. 6 and 7 reveals the formal analogies between human visual classification and machine vision classification. In the image acquisition step, both require good illumination of an object field and optimal positioning with respect to the imaging optics. Both form an image field on photosensitive surfaces having spatially discrete and color-resolving detection elements. And both communicate the image information to a powerful central processor for storage in a large and easily recalled memory. In the subsequent image analysis or pattern recognition step, both compare, analyze, or process the current image information with reference to corresponding image information stored in memory. Measurements or classing calls are made, based on that comparison.

Importantly, the (1) image acquisition and (2) image analysis steps are fundamentally distinct, sequential processes in the human and in the machine vision analogs. Also, image analysis is generally distinct from image reconstruction.

More specifically, an important feature of embodiments of the invention is seen in FIG. 7. Along with the unknown sample (or samples) under test, the object field includes one or more cotton standards whose colors are accurately, precisely and traceably known. Standards produced by USDA/AMS are prepared in boxes containing, typically, six known cottons which are referred to as "biscuits." The reference biscuits are viewed under the same illumination and through the same optical elements as the unknown sample(s) under test. The cotton in the biscuits is generally in the same state and pressed against the windows with the same pressures as the unknowns. The biscuits can be in sealed chambers with inert gases to diminish oxidation and other color-changing causes and thus extend the useful stable color life of the reference biscuits.

The system and method of FIG. 7 thus facilitate matching between unknown cottons and known cottons, or other reference materials. This is because the unknowns and knowns are in the same state and tested with the same optical system at very nearly the same instant in time, thus eliminating illumination, other electro-optical noise and drifts, and positioning errors. This computer-based image analysis and matching is seen to be rigorously analogous to the Classer's physiological actions, as described above and in FIG. 6, in both the image acquisition and image analysis/comparison steps, and in the electronic and in the human "classing call" step.

In an instrument classification embodiment, a high quality color scanner (intended for office or graphics arts use in scanning documents) is employed for image acquisition. About one fourth to one half the object field of 8.5×11 inches (21.59×27.94 cm) is devoted to the reference biscuits and other known reference materials and the other half to the unknown sample(s) under test. Acquired image file sizes, depending on spatial resolution (pixel size) and electronic resolution (bit depth), range in the order of tens of megabytes to several hundred megabytes. Files near the lower end on this size range are acquired and analyzed in less than thirty seconds, currently. Accuracy and precision can approach fundamental limits associated with the color standards used.

The same method can be extended to measurement of trash, including measurement of the color of each trash particle, as well as its shape. This enables classification of bark and grass and other types of foreign matter. Another data product or measurement is preparation via surface texture.

The reference or "target" cottons are formed from universal cotton color standards prepared by the USDA/AMS in Memphis. However, reference cottons from any country, or even from an individual gin or mill, or a mix, may be used for the reference biscuits. Other reference materials can be employed in addition to cottons. This will be important as there is movement toward absolute or Commission Internationale l'Eclairage (CIE) color measurements.

FIGS. 2–5 more particularly depict an embodiment in which color scanner-based image acquisition/analysis technology is adapted to the measurement of cotton Color and Trash. The Ultra-Rapid Conditioning process of module 200 takes place above window 204 in FIGS. 3 and 4. Sample 102 is pressed against window 204 by downward (on perforated plate 212) and upward (on window 204) suction forces explained above. The Color and Trash measurements of module 300 take place below window 204. Color scanner apparatus 302 is attached to the bottom of stable table 111. This stable table 111 is made of aluminum or heavy plastic and is mounting on soft springs (not shown) which are highly damped and which mass-spring-damper system has the purpose of isolating the scanner from vibrations. Conditioned gas flow 115 from conditioner 114 in FIG. 1, which includes filtering, is directed into cabinet 113 to maintain cleanliness of the optical components. Scanner 302 may be a Hewlett-Packard 6000 series scanner or equivalent and includes a scan head 304 which is driven along rails 306 by a stepper motor (not shown). Flexible signal cable 308 connects the several thousand pixel, linear arrays, one for each of the three colors Red, Green and Blue 320, to on-board electronics module 310 which is turn connected to computer 112.

Computer 112 controls scanner 302, acquires and stores its large quantities of data, and operates upon or analyzes these acquired data to generate scientific measurements, which is the functionality of interest in the first embodiment. In another embodiment, computer 112 is used to produce images for human classification, or for communications to other computers, including communications over the internet, where scientific measurements or human classifications can be made.

The processes of: (1) scanning an object field, and acquiring thereby an image file of raw data; and (2) operating upon those acquired raw data to produce a viewable, communicable or analyzable image field, are sequential and very sharply distinct. These processes can be characterized as (1) image acquisition and (2) image reconstruction or recording and reproduction. One analogy is acquisition of a photographic negative from which positive prints are made to reconstruct the image. Another analogy is music recording and subsequent reproduction. Appreciating the nuances of the separate processes of acquisition and analysis or recording and reproduction facilitates understanding the limitations of both processes, including spatial and electronic resolution, dynamic range, various nonlinearities, noise and most particularly, fidelity.

Scanner light source 312 in FIG. 4 illuminates the object field above it 330, FIG. 5, with typical incident rays 313. Incident rays 313 originate directly from elongated lamp 312 or after collection by mirrors 314. Reflected light from object field 330, represented by typical reflected rays 315, hits mirror 316, is collected by lens 318, and imaged onto linear array 320. Stability of the illumination source 312, with respect to intensity in time and in space, and to spectral emissions, is one of the major causes for poor color fidelity. Embodiments of the invention minimize this cause.

For an RGB color scanner with 600 dots/inch (236 dots/cm) or pixels/inch (236 pixels/cm) "optical" resolution and 8.5 inches (21.59 cm) object field width dimension, the number of pixels in the three color channels of linear array 320 is 600×8.5×3=15,300 pixels. For an 11 inch (27.94 cm) length object field with 600 dpi (236 dots/cm) resolution and three colors there are 11×600×3=19,800 pixels. Thus there are 303 million pixels of spatial resolution in the raw image. If the electronic resolution or "bit depth" is 12 bits or 1.5 bytes per pixel, it follows that a 600 dpi (236 dots/cm) resolution scanned color image contains 454 megabytes of data.

Notwithstanding the enormous potential for spatial and electronic resolution in color scanning technology, there are some serious limitations. Scan speed is one of them but that limitation is rapidly disappearing as the technology matures and finds wide application. In the cotton classing context of the invention, fidelity, the inability to faithfully reproduce true colors, with very small variations, is a very serious limitation. When applied to Color and Trash measurement of cotton sample 102 on window 204, currently available scanners 302 (and CCD cameras also) are so severely deficient with respect to fidelity in the recording and reproduction of color images that the technology has not previously been successfully applied to absolute, scientific color measurement. It can be noted that Color and Trash classifications, which are still primarily done by humans, have much higher standards of performance than might be expected. In the field of cotton measurements, color scanner, and CCD camera technology as well, image acquisition and analysis prior to the subject invention have been regarded as hopelessly deficient and inapplicable for cotton classing purposes because of color infidelity. This is particularly true for Colorimetric measurements. Embodiments of the invention overcome this limitation, and set the stage for eliminating human classers, who have their own limitations, in favor of all-instrument classing.

The bottom view of Color and Trash module 300 in FIG. 5 shows that scanned field of view 330 contains, in addition to the unknown sample 102 under test, which sample 102 is pressed against window 204, known reference materials 340, 342, 344, 346. These reference materials are also shown in FIG. 4. Reference material 344, like the others, is positioned above a window 348 that is identical in optical properties to window 204 upon which sample 102 is positioned. The spacings between the scanhead 304 and the reference material windows 348 and sample window 204 are also identical, as are the pressures. Cotton reference materials having traceably known colors, described in greater detail below, are so positioned in fourteen chambers 342, 344. The pressure with which they are loaded is identical with the pressure on the unknown sample 102. The reference or "target" cottons are hermetically sealed within the chambers 342, 344.

The reference cottons are provided by the USDA AMS, Memphis, Tenn. and have precisely known color values assigned to them. By world-wide, between-government treaty agreements, these represent color data originating primarily with the cotton industry and traceable to this one laboratory. Most importantly, these standard cottons are competently and painstakingly produced by well-known methods used for calibrating human cotton classers.

Also seen in object field are other color reference materials such as Munsel papers, portions of industry-accepted color charts such as Kodak Q 60, standardized paints or inks applied to the top of the reference chamber windows 348, or ceramic tiles (because of their long-term stability), and the like. All reference materials are "seen" through windows 348 whose optical properties are also identical.

Use of the reference materials circumvents the multitude of drifts, offsets, nonlinearities, illumination variabilities, misalignments, etc that limit color scanning or CCD camera fidelity. And they can be extended beyond scientific measurement to provide for enhancements in fidelity of color image recording and reproduction in general.

In the disclosed embodiment of the invention for Color and Trash measurements, in module 300 color scanner 302 scans object field 330 which includes unknown sample 102 and reference materials 340, 342, 344, 346. The scanner 302 acquires or records a raw image file for all objects within object field 330 having 8.5×11 inch (21.59×27.94 cm) width and length. Computer 112 operates on the raw recorded data to compare the unknown sample 102 to the known reference materials 340, 342, 344, 346, pixel by pixel if necessary, calculates the best match for Color and, independently, for Trash, and records these measurement data into memory for later use. Examples are measurement and reporting of Color: Rd, +b, and +a of 78.3, 9.3 and 0.13; and Trash: 126 trash particles having 0.16% area fraction and 42% of the particles having equivalent diameters greater than 100 micrometers. These typical Color and Trash readings are according to definitions required by the USDA for the target materials located in chambers 342, 344.

Trash measurements proceed in the same manner as color measurements, wherein reference materials having known percentage areas of leaf and other foreign matter are placed in the object field and subsequently compared to the unknown samples. Care is taken in the preparation of these reference materials that the types of trash and their size distributions are representative of commercial cotton.

It is significant in instrument classification embodiment that scientific measurements can be the end result, not necessarily images with high fidelity, as in the human classification embodiment. Indeed, a limited objective for Color and Trash measurements starts with known USDA Color and Trash data for the known reference or target cottons; the limited objective ends with matching or hitting the targets of these USDA-generated values, as disclosed above.

Thus, no image of the test cotton need be displayed for the scientific tests disclosed herein. However, satisfactory results for both matching the internal targets, for Color and Trash measurements, and for producing viewable and analyzable images, for human and for automated classing, can be obtained when standard paints are applied to the top side of windows 340, 346 and for which paints the scientific colors are determinable and stable. This means that our apparatus and methods and system can be applied to more rigorous, absolute color measurements. Accordingly, our methods and apparatus, which embrace the two types of absolute, instrumental color referencing to traceable materials in chambers 340, 346 and to "accepted" materials with "accepted" Colorimetric targets values in chambers 342, 344, along with unknown samples 102 in identical optical environments 330, can be extended to enhance fidelity in the recording and reproduction of images for measurement purposes in general.

It will be appreciated that embodiments of the invention rely upon the availability of advanced digital technologies for high resolution, high quality, color image acquisition, storage, processing, and communication. One salient feature is very large digital files. One such color image file, acquired with maximum resolution available now, can contain as many megabytes of data as all of the currently-reported HVI data on one million bales. Of course, these large image files are analyzed and reduced to data products representing scientific measurements which are only a few bytes in length.

Figure 12:
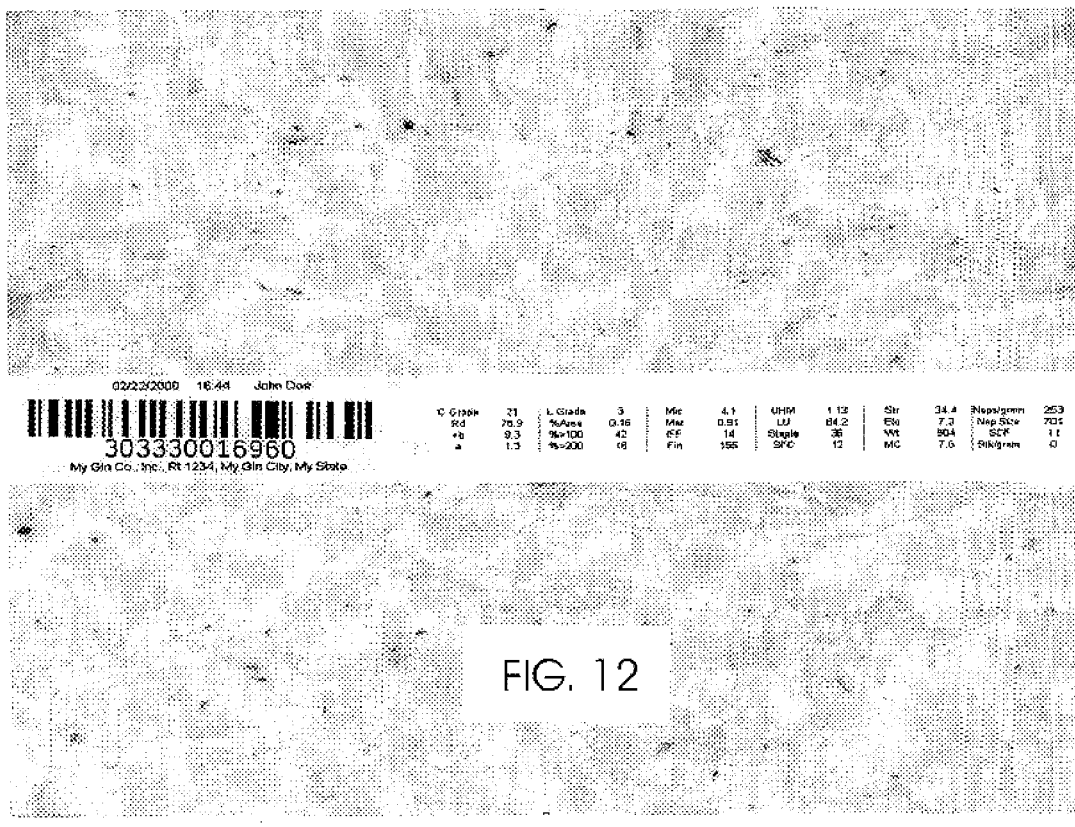
FIG. 12 is an image of a cotton sample acquired by an embodiment of the invention.

FIGS. 8–11 indicate the levels of performance achieved in the instrument classification embodiment. Scientific readings produced very favorably compare with the USDA/AMS results for Color and Trash reference materials, over a wide range of color and trash values. FIG. 12 is a composite image containing an image of both samples from a bale and an overlay of the scientific measurements for the bale having the indicated permanent bale identification bar code. It may be appreciated that our scientific measurements are obtained with the new technologies and methods herein disclosed whereas the reference readings are based on very old, known technologies. Particular attention is drawn to FIG. 11 which compares the color readings of our methods, marked STI, with conventional HVIs A, B and C, all in different laboratories but in a round test using the same reference cotton samples. USDA tolerances of +/−1 unit in Rd and +/−0.5 unit in +b are represented by the boxes. It is clearly seen that the STI data re within the tolerance boxes more frequently than conventional HVI.

To summarize the procedural steps for producing scientific measurements of color and trash by our invention, given a calibrated apparatus including known reference materials:

1. Acquire an image file of the unknown sample under test along with known reference materials in a single object field;
2. Apply color and trash matching algorithms in an image analysis step so that the internal computer interpolates the measurements and makes the classification "call."

Internet Classing

Cotton Classing takes on or will take on two primary forms or transitional combinations thereof:

A. Traditional Classing. Collect samples and ship them to remote sites for human and/or instrument classing. Archivally store many physical samples remotely and the data in data base(s); and B. Internet Classing. Execute instrumental classing locally (in gins, warehouses, or mills) and transfer the fiber quality measurements, including images, over the Internet. Archivally store few samples for calibration confirmations and all data, including images, in databases.

One transitional combination of Traditional and Internet Classing, begins with acquisition of images, along with other fiber quality data, at the gin. These data and images are then transferred over the Internet for classification and other judgements and decisions, such as buy/sell decisions, by humans. Thus a human classification is made by classers looking at a high fidelity reproduction of the image file on an image display device such as a high quality color video monitor.

To better appreciate performing cotton classing and selling/buying cotton over the Internet, operation of the instrument 100 is here briefly described: An operator removes the two cut samples from the two bale sides and places both samples on the Color and Trash scanning window. The operator starts the testing process, and the instrument then automatically completes the chosen fiber quality tests which can include, color, trash, micronaire, length, strength, neps and stickiness, for example. Each sample is internally conditioned to 65% RH and 21° C., standard laboratory conditions. The image and associated fiber quality data are then sent to a local network for viewing by the ginner, and then to the Internet to be viewed by potential buyers or the producers.

The image of FIG. 7 displays both classers' samples with their associated fiber quality measurements. Other data may be attached to inform the potential buyer of relevant information to make a purchasing decision.

Figure 13:
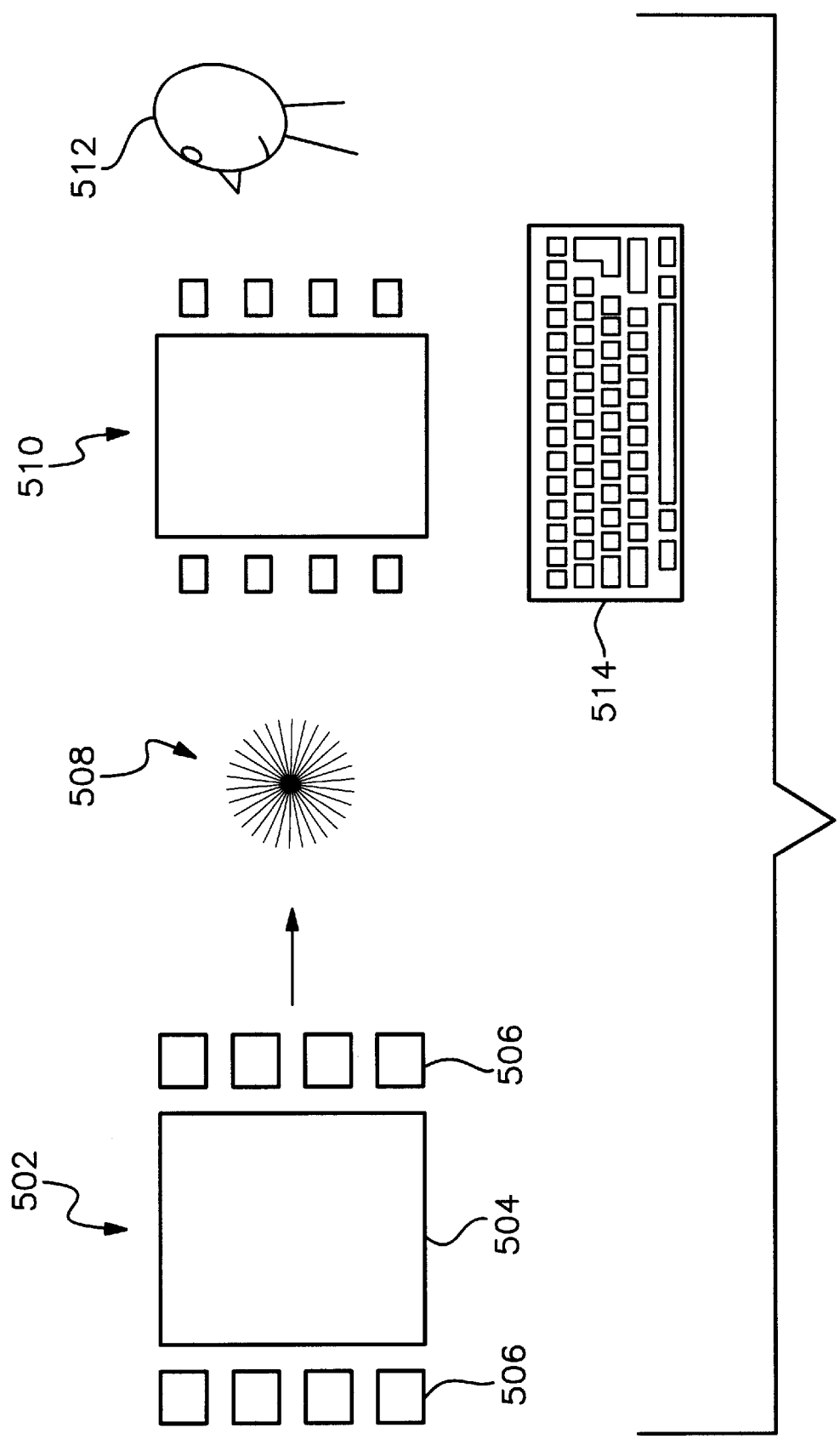
FIG. 13 shows a pattern of reference biscuits.

Again, an important feature of embodiments of the invention is inclusion of known reference materials, especially cottons for this embodiment, in the object field of view. The primary commercial purpose for this "Internet Classing" embodiment is to enable communication of the acquired image files over the Internet with subsequent remote classification. By "Internet Classing" 500 in FIG. 13 we mean, procedurally:

1. acquisition of raw image files of object field 502 at one location, including unknown sample under test 504 and one or more known reference materials 506 in the object field;
2. communication of these files over the Internet 508 to one or more computers at one or more remote locations which reconstruct, with high fidelity, images 510 of the original object field 502; and
3. observation of the reconstructed images by trained human observers or "Cotton Classers 512."

Most importantly, human observers 512 see a reconstructed image field containing the sample under test and the standard reference materials. This means that unavoidable distortions, nonlinearities and noise in the acquisition, communication, and reconstruction steps affect both the unknown sample under test and the known reference material.

The acquisition of raw image files of the object field is precisely the same as described for the first embodiment and is further described in FIG. 7.

In another embodiment, scientific measurements can be made by a computer processor at the remote location, operating on the digital image file, without necessarily displaying it.

A few clarifying comments now complete the disclosure. Whereas the original object field 502 and reconstructed image field 510 are seen to have eight square reference biscuits 506 surrounding the square sample under test 504, it will be appreciated that the number and shape of reference biscuits and the size and shape of the sample under test may be chosen to suit the particular preferences of the user. For some applications, linear strips of reference material are advantageous.

Although our methods make human classification from a color monitor possible, the monitor used to reconstruct the images 510 should preferably be high fidelity and calibrated and it should preferably be situated in an appropriate viewing environment. It will be appreciated that human classification of passively reflected light from a physical sample versus actively emitted light from a monitor are fundamentally different. Without inclusion of known reference materials in the recording and reconstruction steps, human classification from a monitor would not be possible.

Figure 14:
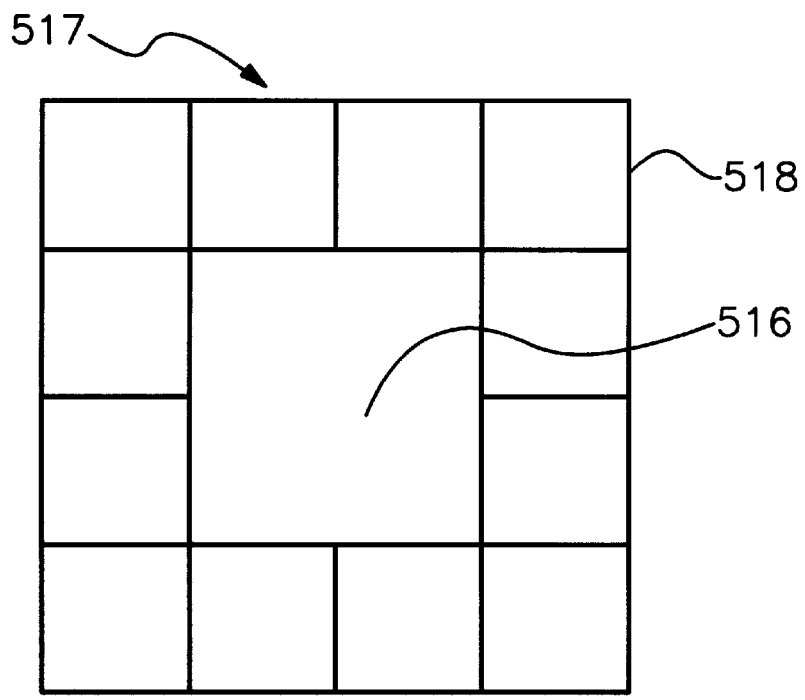
FIG. 14 shows interpolated reference biscuits.

It will be appreciated that discerning small color and trash differences is not easy, physiologically or psychologically, and all of the "tricks" of modern pattern recognition must be employed to facilitate the human judgement call. Note again the eight reference biscuits 506 seen in FIG. 13; their primary purpose is to accommodate the distortions, nonlinearities and noise of real-world color recording and reproduction apparatus over a wide range of colors. We have found that interpolations in reconstruction can enable generation of a much larger set of equivalent reference materials with a narrower range of color differences in images having different shapes. Thus the human Classer 512 in FIG. 13 would determine that the color of the unknown sample lies between that of a few of the knowns. He or she would then cause the computer, via keyboard 514 or other control means to produce interpolated biscuits with narrower color range in a pattern 517 as seen in FIG. 14. The unknown sample's image is in the center and the interpolated reference biscuits 518 surround it, from which a more accurate and precise color call is made.

Figure 15:
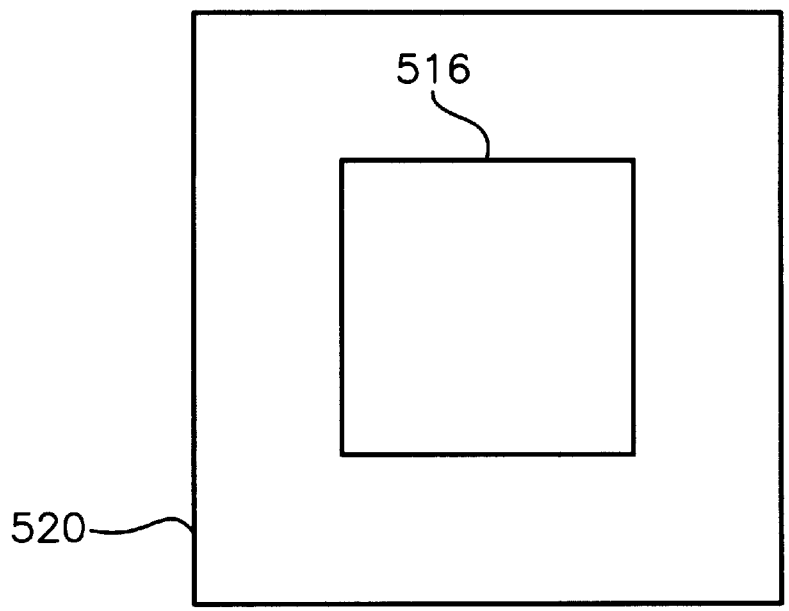
FIG. 15 shows an interpolated image.

Another color pattern recognition tool is seen in FIG. 15 where the unknown image is surrounded by an interpolated image 520 whose color coordinates may be varied by the Classer until a match is realized. We have found that this "trick" is particularly useful for human cotton classing. However, we have also found that the computer can surpass the human, when the matching is automated.

We note finally that the communicated digital image files may be analyzed remotely as well as be reconstructed for human viewing. That is, since the digital communication is almost error free, and since transfer of tens to hundreds of megabyte files is increasingly feasible, the image analysis from which scientific data products are produced may take place remotely and at any later time. This capability enables different analytical procedures to be employed. For example, the general algorithms by which conventional "HVI" color and trash measurements are generated at one location may not serve the specific purposes of certain Customers at other locations, who could execute unique algorithms better matched to their requirements. This is particularly important for international commerce, since the standards used by sellers and buyers in different countries are generally different.

We further note in conclusion that embodiments of the invention provide for local viewing by humans and for viewing aids such as magnification and various pattern recognition enhancements known in the art.

While specific embodiments of the invention have been illustrated and described herein, it is realized that numerous modifications and changes will occur to those skilled in the art. It is therefore to be understood that the appended claims are intended to cover all such modifications and changes as fall within the true spirit and scope of the invention.

What is claimed is:

1. A system for acquiring an image for classifying an unknown sample of cotton, said system comprising:
   an optical imaging device having a defined object field of view;
   an element for positioning the unknown sample of cotton in the object field of view; and
   at least one reference material in the object field of view;
   whereby said optical imaging device acquires images of both the unknown sample of cotton and the reference material in the same field of view.

2. The system of claim 1, wherein said optical imaging device comprises a scanner intended for scanning documents.

3. The system of claim 1, wherein said reference material is selected from the group consisting of cotton standards, Munsel papers, color charts, standardized paints, and ceramic tiles.

4. The system of claim 1, wherein said optical imaging device outputs a digital image file.

5. A system for classifying an unknown sample of cotton, said system comprising:
- an optical imaging device having a defined object field of view;
- an element for positioning the unknown sample of cotton in the object field of view such that said optical imaging device acquires an image of the unknown sample;
- at least one reference material in the object field of view such that said optical imaging device acquires an image of the reference material in the same field of view as the image of the unknown sample; and
- a processor connected to receive a digital image file from said optical imaging device and operable to compare data corresponding to the image of the unknown sample with data corresponding to the image of the reference material to determine a cotton color measurement.

6. The system of claim 5, which further comprises a storage device for storing the digital image file for subsequent reconstruction and viewing.

7. The system of claim 5, wherein:
- there are a plurality of cotton standards as reference materials in the object field of view; and wherein
- said processor is operable to compare data corresponding to the image of the unknown sample with data corresponding to images of the reference materials to determine the closest match.

8. The system of claim 5, wherein:
- there are a plurality of color samples as reference materials in the object field of view; and wherein
- said processor is operable to determine a color calibration from images of the reference materials and to adjust data corresponding to the images of the unknown sample in view of the color calibration to determine color values.

9. The system of claim 5, wherein said optical imaging device comprises a scanner intended for scanning documents.

10. The system of claim 5, wherein said reference material is selected from the group consisting of cotton standards, Munsel papers, color charts, standardized paints, and ceramic tiles.

11. The system of claim 5, wherein said processor is co-located with said optical scanning device.

12. The system of claim 5, wherein said processor is located remotely from said optical scanning device.

13. The system of claim 5, wherein said processor is further operable to measure trash within the unknown sample.

14. The system of claim 5, wherein said processor is further operable to measure preparation of the unknown sample.

15. A method for classifying an unknown sample of cotton, said method comprising:
- employing an optical imaging device to acquire, within the same object field of view, an image of the unknown sample of cotton and an image of at least one reference material; and
- employing a processor to compare data corresponding to the image of the unknown sample with data corresponding to the image of the reference material to determine a cotton color measurement.

16. A system employing a computer network for classifying an unknown sample of cotton, said system comprising:
- an optical imaging device having a defined object field of view;
- an element for positioning the unknown sample of cotton in the object field of view such that said optical imaging device acquires an image of the unknown sample;
- at least one reference material in the object field of view such that said optical imaging device acquires an image of the reference material in the same field of view as the image of the unknown sample; and
- a connection via the computer network for transmitting a digital image file from said optical imaging device representing the object field of view to a remote location.

17. The system of claim 16, which further comprises an image display device at the remote location whereby a human observer can classify the cotton by comparing an image of the unknown sample with an image of the reference material.

18. The system of claim 16, which further comprises a processor at the remote location connected to receive the digital image file from said optical imaging device and operable to compare data corresponding to the image of the unknown sample with data corresponding to the image of the reference material to determine a cotton color measurement.

19. A method for classifying an unknown sample of cotton, said method comprising:
- employing an optical imaging device to acquire, within the same object field of view, an image of the unknown sample of cotton and an image of at least one reference material;
- constructing a digital image file representing the images; and
- transmitting the digital image file via a computer network to a remote location.

20. The method of claim 19, which further comprises employing an image display device at the remote location to display images of the unknown sample and the reference material in the same field of view whereby a human observer can classify the cotton by comparing the images.

21. The method of claim 19, which further comprises employing a processor at the remote location to compare data corresponding to the image of the unknown sample with data corresponding to the image of the reference material to determine a cotton color measurement.

* * * * *